(12) United States Patent
Takemoto

(10) Patent No.: US 6,354,338 B1
(45) Date of Patent: Mar. 12, 2002

(54) ICING ARTICLE, APPARATUS FOR SUPPLYING THE SAME, AND METHOD FOR OPERATING THE APPARATUS

(76) Inventor: Yoshinori Takemoto, 1-11-41, Tsukimino, Yamato-shi, Kanagawa-ken (JP)

( * ) Notice: Subject to any disclaimer, the term of this patent is extended or adjusted under 35 U.S.C. 154(b) by 0 days.

(21) Appl. No.: 09/451,126

(22) Filed: Nov. 30, 1999

(30) Foreign Application Priority Data

Dec. 8, 1998 (JP) ............................................ 10-366066
Jan. 29, 1999 (JP) ........................................... 11-021280
Oct. 15, 1999 (JP) ........................................... 11-293364

(51) Int. Cl.⁷ ................................................. A61F 7/10
(52) U.S. Cl. ............................... 141/82; 141/9; 141/10; 141/166; 141/313; 141/314; 53/127; 53/440
(58) Field of Search ................................ 141/9, 10, 82, 141/103, 104, 166, 313, 314, 317; 53/127, 440

(56) References Cited

U.S. PATENT DOCUMENTS

| | | | | | |
|---|---|---|---|---|---|
| 3,698,451 | A | * | 10/1972 | Hudson | 141/166 |
| 4,049,154 | A | * | 9/1977 | Burks | 221/76 |
| 4,132,049 | A | * | 1/1979 | Mullins, Jr. | 53/452 |
| 4,587,810 | A | * | 5/1986 | Fletcher | 62/3 |
| 5,005,364 | A | * | 4/1991 | Nelson | 62/76 |
| 5,079,897 | A | * | 1/1992 | Muller | 53/284.7 |
| 5,088,300 | A | * | 2/1992 | Wessa | 62/340 |
| 5,112,477 | A | * | 5/1992 | Hamlin | 210/85 |
| 5,277,016 | A | * | 1/1994 | Williams et aol. | 53/459 |
| 5,581,982 | A | * | 12/1996 | Schroeder et al. | 53/459 |
| 5,619,841 | A | * | 4/1997 | Muise et al. | 53/440 |
| 6,093,312 | A | * | 7/2000 | Boulter | 210/86 |
| 6,112,539 | A | * | 9/2000 | Colberg | 62/331 |

* cited by examiner

*Primary Examiner*—J. Casimer Jacyna
(74) *Attorney, Agent, or Firm*—Jiawei Huang; J.C. Patents

(57) ABSTRACT

There is provided an apparatus for supplying an ice water-containing bag for use in icing. The apparatus includes an ice machine, an ice storing section for storing ice manufactured by the ice machine, ice packing means for packing the ice stored in the ice storing section in a bag having a water resistance, water supplying means for supplying water into the bag, sealing means for sealing an opening of the bag in which ice and water has been put, a belt conveyer for carrying the bag containing ice and water, a controller for controlling the respective means to be activated/suspended, and ice-water manufacturing instructing means connected with the control means, for sending an instruction for manufacturing the ice water-containing bag.

4 Claims, 2 Drawing Sheets

ICING ARTICLE, APPARATUS FOR SUPPLYING THE SAME, AND METHOD FOR OPERATING THE APPARATUS

BACKGROUND OF THE INVENTION

1. Field of the Invention

The present invention relates to an icing article, an apparatus for supplying the same, and a method for operating the apparatus.

2. Background Art

It is known that fatigue of overwork muscles by exercises can be easily recovered by cooling them with ice (hereinafter called "icing"). General icing method which is carried out at present is to put a required amount of ice manufactured by an ice machine into a bag with water, close its opening with a rubber band to prevent water from leaking, and hold it to a portion to be recovered to cool muscles for recovery. The reason why water is used with ice is to prevent skin from frostbiting clue to the excessive decrease in temperature only by ice. Thus, normally it is used by mixing ice with water.

However, icing which is considered to have an effect for recovering fatigue of overwork muscles is still not popularized. The main factor by which icing is still not popularized is that it is troublesome to prepare a packed ice water each time. Thus, there is a certain need to provide an apparatus for supplying a packed ice water in a simple and inexpensive way.

Further, there is need to prevent icing carried out by means of a bag containing only ice from becoming disorder such as frostbiting.

There is another way to recover muscles by various items for icing which comprise some chemicals received in isolation and use an endothermic reaction by contacting the chemicals with each other when used However, there is a hazard to cause frostbite due to the excessive decrease in temperature. Further, since such an item for icing with chemicals is expensive, it would be useful for medical treatment of a sprain or the like, but is not suitable for daily use for recovery of overwork muscles. Therefore, it has never been used for the purpose of recovery of overwork muscles before being injured.

SUMMARY OF THE INVENTION

The present invention has been achieved in view of such problems in the prior art, and an object of the present invention is to provide an apparatus for supplying an ice water-containing bag, comprising ice manufacturing means for manufacturing a required amount of ice, ice packing means for putting the ice manufactured by said ice manufacturing means into a bag having a water resistance; water supplying means for supplying water into said bag; sealing means for sealing an opening of said bag in which ice and water has been put; control means for controlling the respective means to be activated/suspended; and ice-water manufacturing instructing means connected with the control means, for sending an instruction for manufacturing the ice water-containing bag.

According to the present invention, since the ice-water containing bag can be supplied simply by operating the ice-water manufacturing instructing means, one who needs icing can easily and promptly obtain the ice-water containing bag.

Furthermore, the ice-water containing bag supplied by the apparatus according to the present invention can be made cheaper than the icing article using some chemicals and may easily be discarded, and thus it can be used comfortably in a school or the like. In addition, it becomes possible to easily recover fatigue of overwork muscles by exercises by applying the ice-water containing bag according to the present invention, thereby preventing one from being injured due to his fatigue of muscles.

Besides, in the apparatus for supplying an ice water-containing bag as above, a bag keeping section for keeping a plurality of bags may preferably be comprised. Alternatively, the apparatus may comprise bag manufacturing means.

In the apparatus comprising the bag keeping section, there is no need to provide another bag manufacturing means and the apparatus itself may be made smaller in size, On the other hand, in the apparatus comprising the bag manufacturing means, there is no need to buy bags for containing ice water and it becomes possible to reduce a running cost.

A further object of the present invention is to provide a method for operating an apparatus for supplying an ice water-containing bag according to any one of the above ones, the method comprising the steps of: placing a bag; putting a predetermined amount of ice into the bag; pouring a predetermined amount of water into the bag containing ice upon receipt of an instruction signal output from an ice-water manufacturing instructing means by operating water supplying means; and closing an opening of the bag by sealing means. According to the invention, since the bag is placed with having already contained ice, the supplement of ice water-containing bag can be achieved more promptly.

Furthermore, still another object of the present invention is to provide an icing article comprising a bag having a watar resistance and a predetermined amount of ice contained in the bag and having a temperature above −10° C.

In addition, another object of the present invention is to provide an apparatus for supplying an ice-containing bag for icing, comprising: ice manufacturing means for manufacturing a required amount of ice; ice packing means for putting the ice manufactured by said ice manufacturing means into a bag having a water resistance and sealing the bag; an ice-containing bag storing portion for storing a plurality of ice-containing bag prepared by said ice packing means in a temperature range of −10° C.–0° C.; discharging means for discharging the ice-containing bag stored in the ice-containing bag storing portion; and discharge instructing means for activating the discharging means to discharge the ice-containing bag.

According to the icing article of the present invention, since the temperature of the ice contained in the bag is made being a temperature above −10° C., a part of ice contained in the bag is rapidly melted by flushed body after exercise, thereby providing water in the bag together with ice. After that, body is cooled by water of 0° C. via the bag to prevent skin from suffering low-temperature injury, such as frostbiting.

BRIEF DESCRIPTION OF THE DRAWINGS

These and other objects and advantages of the present invention will become clear from the following description with reference to the accompanying drawings, wherein.

DETAILED DESCRIPTION OF THE PREFERRED EMBODIMENTS

The first embodiment according to the present invention will be described hereinafter with reference to FIG. 1.

Figure 1:
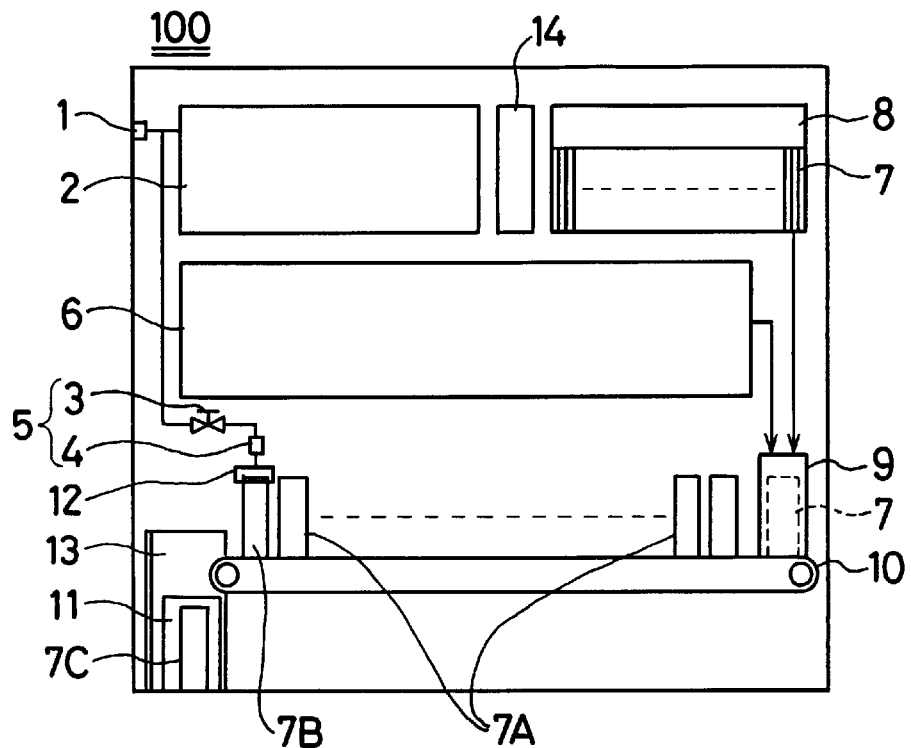
FIG. 1 is a schematic view showing a first embodiment according to the present invention.

In FIG. 1, reference numeral 100 designates an apparatus for supplying a packed ice water according to the present invention. The apparatus 100 is provided with a water taking-in opening 1 which is connected to a public water supply (not shown) or the like to take in tap water. The water taking-in opening 1 is connected with an ice machine 2 and water supplying means 5. The ice machine 2 is known and mounted on an upper portion of the apparatus 100. The water supplying means 5 is composed of an open/close valve 3 and a water supplying opening 4 and is installed in a middle portion of the apparatus 100.

Below the ice machine 2 an ice storing section 6 is provided, for storing ice (not shown) manufactured by the ice machine 2. Beside the ice machine 2, a bag keeping section 8 for keeping a plurality of bags 7 having a water resistance is provided. Below the ice storing section 6 and the bag keeping section 8, at the opposed side of the water supplying means 5 ice packing means 9 is installed. The ice packing means 9 has functions for taking out the bag 7 from the bag keeping section 8 one by one and for packing a predetermined amount of ice from the ice storing section 6 in the bag 7 taken out.

Reference numeral 10 designates a belt conveyer which functions as conveying/carrying-out means and is driven by a motor not shown. The length of the belt conveyer 10 is a length sufficient for placing a predetermined number, e.g. 10 to 30, of bags 7A which have contained ice by the ice packing means 9 side by side. A starting end of the belt conveyer 10 is arranged just below the ice packing means 9 and a distal end of the conveyer 10 is arranged just above a discharging opening 11 via a place under the water supplying means 5. The belt conveyer 10 can convey the ice-containing bags 7A below the water supplying means 5 and also can convey bags 7C (described hereinafter) above the discharging opening 11. Still further, the respective openings of the ice-containing bags 7A placed on the belt conveyer 10 side by side are made opened by bag opening means not shown at least just below the water supplying means 5.

Besides, a predetermined amount of water is poured into the bag 7A by the water supplying means 5 to prepare the bag 7B containing a predetermined amount of ice and water. In order to seal the opening of the thus prepared bag 7B at the same place where the water is poured or downstream side, sealing means 12 is installed, which is known in the art, such as a heat sealer or the like. Still further, reference numeral 13 designates a shooter, an upper section of which is located at the end of the belt conveyer 10 and a lower section of which is located at the discharging opening 11. The shooter 13 can guide the sealed ice water-containing bag 7C conveyed by the belt conveyer 10 to the end of the conveyer 10 smoothly into the discharging opening 11.

Reference numeral 14 designates a controller for controlling the apparatus, which stores a predetermined controlling program for actuating the ice machine 2 composed of a compressor, a condenser, an evaporator or the like, or Peltier element, or the like, manufacturing ice having a predetermined size from water taken in from the water taking-in opening 1, and storing a required amount of ice in the ice storing section 6.

Besides, the controller 14 also stores a preset controlling program for actuating the ice packing means 9, taking out a bag 7 from the bag keeping section 8 one by one, putting a predetermined amount of ice stored in the ice storing section 6 into the bag 7 took out, placing a predetermined number of the ice-containing bags 7A on the belt conveyer 10 at the upstream side of the water supplying means 5, pouring a predetermined amount of water into the ice containing bag 7A just below the water supplying means 5 from the water supplying opening 4 by opening the open/close valve 3 during a predetermined time interval upon received an instruction from ice-water manufacturing instructing means (not shown, hereinbelow simply called as "operation switch") provided in the front panel or the like of the apparatus, closing the opening of the ice-water containing bag 7B by actuating the sealing means 12, dropping the thus prepared ice-water containing bag 7C from the end of the belt conveyer 10 by rotating a motor of the belt conveyer 10 in a predetermined number, thereby moving the bag 7C from the discharging opening 11 via the shooter 13 in a required distance, while supplementing an ice-containing bag 7A by actuating the ice packing means 9 on the belt conveyer 10.

In the apparatus as constructed above, since the ice-water containing bag 7C is supplied from the discharging opening 11 simply by operating the operation switch, one who needs icing can easily and promptly obtain the ice-water containing bag 7C.

Figure 2:
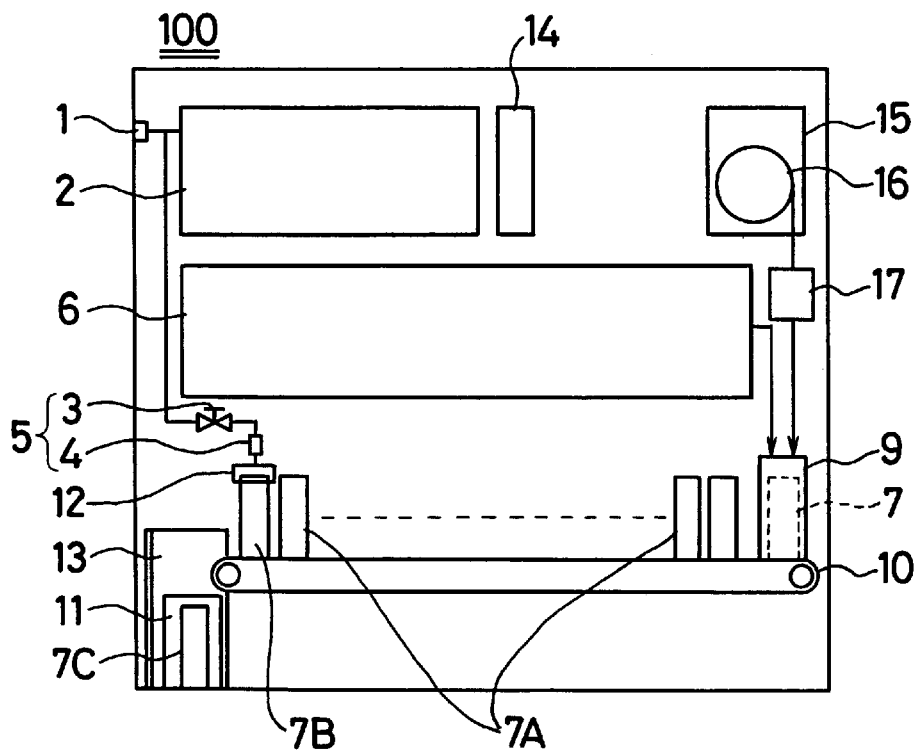
FIG. 2 is a schematic view showing a variation of the first embodiment according to the present invention.

Besides, as shown in FIG. 2, instead of the bag keeping section 8 a wound sheet keeping section 15 may be provided. In this case, the wound sheet keeping section 15 can keep a sheet 16 having a heatsealability and water resistance as a roll shape by winding or zigzag winding the sheet in a tube form, a folded form, or a double-layered form. The end of the roll is drawn out therefrom and sealed at a portion to be formed as a bottom portion and/or as a side overlapping portion by pressing a heat sealing bar or by applying ultrasonic to thereby form it as a bag preform as well as cut off. After then, the bag preform is shaped into a bag by known bag manufacturing means 17. Then the resulted bag is packed with ice stored in the ice storing section 6 by the ice packing means 9.

Figure 3:
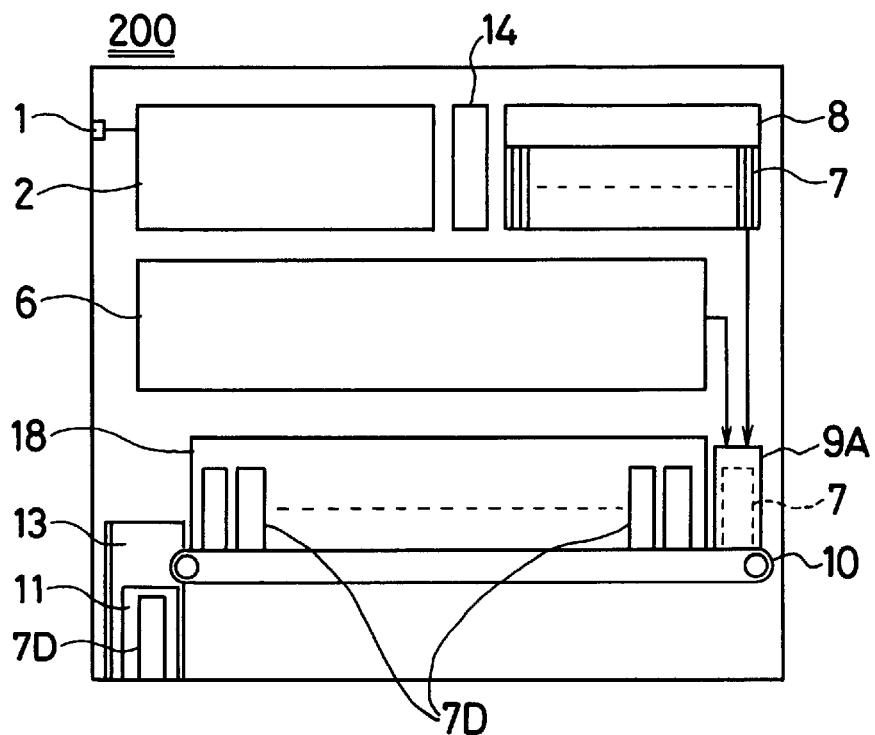
FIG. 3 is a schematic view showing a second embodiment according to the present invention.

Next, the second embodiment according to the present invention will be described in detail with reference to FIG. 3. In this embodiment, the same reference numerals and symbols identical to those in the first embodiment designate the same meaning.

An apparatus 200 for supplying a packed ice is not provided with the water supplying means 5 which is mounted in the aforesaid apparatus 100 for supplying a packed ice water. Reference numeral 9A designates ice packing means having functions for taking out the bag 7 from the bag keeping section 8 one by one, for packing a predetermined amount of ice from an ice storing section 6 in the bag 7 taken out, and for sealing the opening thereof by a known sealing technique.

Reference numeral 18 designates an insulating box member for covering a plurality of sealed ice-containing bag 7D placed on the belt conveyer 10. The insulating box member 18 has doors not shown at a place facing to the ice packing means 9A and a place facing to the shooter 13, which can be freely opened and closed. Furthermore, cooled air or the like can be fed from a cold heat generating portion or the like of the ice machine 2 for generating cold heat for manufacturing ice to the inside or the circumference of the insulating box member 18, thereby setting the inside temperature of the insulating box member 18 which is a storing portion for the ice-containing bags 70 to a required temperature range of −10° C.–0° C. In this case, the temperature is set to, for example, −2° C. which is just below the melting point of ice.

Furthermore, the controller 14 for controlling the apparatus 200 for supplying a packed ice can store a predetermined control program which controls the activation of the ice machine 2, the manufacturing of ice having a predetermined size from water supplied from the water taking-in opening 1, and the storing amount of ice in the ice storing section 6. In addition, the controller 14 can also control the amount of cold heat to be generated by the cold heat generating portion of the ice machine 2 so as to make the ice temperature manufactured in the ice machine 2 become a temperature range of −10° C.–0° C., for example, around −5° C.

Besides, the controller 14 stores and carries out a prescribed program for activating the ice packing means 9A to take out the bag 7 from the bag keeping section 8 one by one, pack a predetermined amount of ice from an ice storing section 6 in the bag 7 taken out, and seal the opening of the bag 7, placing a predetermined number of the ice-containing bags 7D placed on the belt conveyer 10 covered by the insulating box member 18, dropping the thus prepared respective ice-containing bag 7D from the end of the belt conveyer 10 by rotating a motor of the belt conveyer 10 in a predetermined number after opening the doors at the both ends of the insulating box member 18 upon operating of ice-containing bag discharging instructing means (not shown, hereinbelow simply called as "operation switch") provided in the front panel or the like of the apparatus 200, thereby moving the bag 7D from the discharging opening 11 via the shooter 13 in a required distance, while supplementinq an ice-containing bag 7D by actuating the ice packing means 9A on the belt conveyer 10.

In the apparatus 200 for supplying a packed ice constructed above, since simple operation of the operation switch activates the system to rapidly discharge the ice-containing bag 7D from the discharging opening 11, one who needs icing can easily and promptly obtain the ice-containing bag 7D.

In addition, the ice contained in the ice-containing bag 7D discharged from the discharging opening 11 is manufactured by the ice machine 2, of which temperature is kept at −5° C., and enclosed in the bag 7 by the ice packing means 9A followed by keeping it inside the insulating box member 18 of which temperature is controlled around −2° C., near the melting point of ice. Accordingly, if icing is carried out by using this ice-containing bag 7D, it is possible to prevent skin from suffering low-temperature injury, such as frostbiting or the like.

Namely, a part of ice contained in the bag is rapidly melted by flushed body after exercise, thereby providing water in the bag together with ice. After that, body is cooled by water of 0° C. via the bag to prevent skin from suffering low-temperature injury, such as frostbiting.

Figure 4:
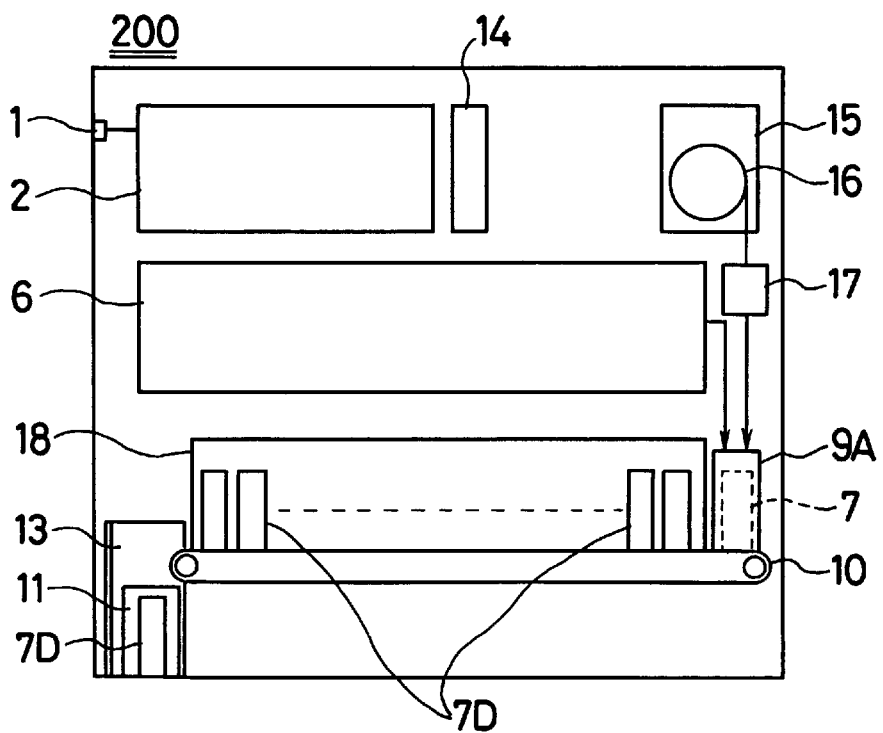
FIG. 4 is a schematic view showing a variation of the second embodiment according to the present invention

Besides, in the apparatus 200 for supplying a packed ice, as shown in FIG. 4, instead of the bag keeping section 8 a wound sheet keeping section 15 may be provided and a sheet 16 having a heatsealability and water resistance kept by the wound sheet keeping section 15 may be shaped into a bag 7 by the bag manufacturing means 17. Then the resulted bag is packed with ice stored in the ice storing section 6 by the ice packing means 9A.

Besides, the present invention is not limited to the above mentioned embodiments and various changes and modifications may be made by those skilled in the art without departing from the scope of the invention as set forth in the appended claims.

For example, the apparatus may be constructed such that an insertion opening for a coin, a bank note, a credit card, a prepaid card at the like may be provided and in a case where a predetermined amount of money or money presentation is provided the operation switch for supplying an ice water-containing bag 7C or art ice-containing bag 7D can properly be functioned.

Furthermore, a number designation switch for designating the number of bags to be supplied may be provided. For example, when one selects five ice water-containing bag 7c or ice-containing bag 7D by actuating the number designation switch, the apparatus can supply the requested number of bags.

Besides, in the apparatus 200 for supplying a packed ice, the temperature of ice manufactured by the ice machine 2 and the temperature inside the insulating box member 18 may be appropriately selected depending on a place where the apparatus is installed.

Namely, in a case where the apparatus 200 for supplying a packed ice is installed at an elementary school or junior high school, the aforesaid temperatures may be closed to the ice melting point because a body of a school boy/girl to be cooled tends to be overcooked due to his/her relatively small heat capacity.

On the other hand, in a case where the apparatus 200 for supplying a packed ice is used for an apparatus for supplying an icing good for adult, a body of adult does not tends to be overcooled due to its relatively large heat capacity. Since the ice packed in the bag tends to be easily melted, when the aforesaid temperatures are set to be closed to the ice melting point, the ice packed in the bag is melted for a short period of time and there is the apprehension that effect of icing is disappeared rapidly. To cope with the problem, the aforesaid temperatures may be set in remote temperature from the melting point of ice. In this case, since there is possibility to suffer low-temperature injury, it should be noted that the temperature may preferably be set above −10° C.

Furthermore, in the apparatus 200 for supplying a packed ice for both of child and adult, in order to prevent child's skin from suffering low-temperature injury the aforesaid temperatures may be set to be closed to the melting point of ice (for example −5° C. or more, preferably −3° C. or more), while in order that co-presence state of ice and water can be maintained at least for 15 minutes in a case that an adult uses, the amount of ice to be packed in the bag 4 may be made larger (for example, 150 g or more) and packed.

What is claimed is:

1. An apparatus for supplying an ice water-containing bag, comprising:

ice manufacturing means for manufacturing a required amount of ice;

ice packing means for putting the ice manufactured by said ice manufacturing means into a bag having a water resistance;

water supplying means for supplying water into said bag;

sealing means for sealing an opening of said bag in which ice and water has been put;

control means for controlling the respective means to be activated/suspended; and ice-water manufacturing instructing means connected with said control means, for sending an instruction for manufacturing said ice water-containing bag.

2. The apparatus for supplying an ice water-containing bag according to claim 1, wherein said apparatus further comprises a bag keeping section for keeping a plurality of bags.

3. The apparatus for supplying an ice water-containing bag according to claim 1, wherein said apparatus further comprises bag manufacturing means for manufacturing a bag from a sheet.

4. A method for operating an apparatus for supplying an ice water-containing bag according to any one of claims 1 to 3, said method comprising the steps of:

placing a bag;

putting a predetermined amount of ice into the bag;

pouring a predetermined amount of water into the bag containing ice upon receipt of an instruction signal output from an ice-water manufacturing instructing means by operating water supplying means; and closing an opening of the bag by sealing means.

* * * * *